United States Patent
Oh et al.

(10) Patent No.: US 12,227,478 B2
(45) Date of Patent: Feb. 18, 2025

(54) PROCESSES FOR PREPARING (3R,4R)-1-BENZYL-N,4-DIMETHYLPIPERIDIN-3-AMINE OR A SALT THEREOF AND PROCESSES FOR PREPARING TOFACITINIB USING THE SAME

(71) Applicant: YUHAN CORPORATION, Seoul (KR)

(72) Inventors: Sang-Ho Oh, Gunpo-si (KR); Doo-Byung Lee, Yongin-si (KR); Kyoung-Chan Kwon, Hwaseong-si (KR); Sang-Won Kim, Hwaseong-si (KR); Hyo-Ick Hwang, Suwon-si (KR); Kyeong-Sill Lee, Hwaseong-si (KR); Ik-Su Jo, Osan-si (KR); Ji-Hye Choi, Suwon-si (KR); Sung-Hee Cho, Suwon-si (KR); Su-Young Lee, Hwaseong-si (KR)

(73) Assignee: YUHAN CORPORATION, Seoul (KR)

( * ) Notice: Subject to any disclaimer, the term of this patent is extended or adjusted under 35 U.S.C. 154(b) by 724 days.

(21) Appl. No.: 17/594,062

(22) PCT Filed: Apr. 3, 2020

(86) PCT No.: PCT/KR2020/004547
§ 371 (c)(1),
(2) Date: Sep. 30, 2021

(87) PCT Pub. No.: WO2020/204647
PCT Pub. Date: Oct. 8, 2020

(65) Prior Publication Data
US 2022/0144774 A1    May 12, 2022

(30) Foreign Application Priority Data

Apr. 5, 2019  (KR) .......... 10-2019-0040383

(51) Int. Cl.
C07D 211/56    (2006.01)
C07D 487/04    (2006.01)
(52) U.S. Cl.
CPC .......... *C07D 211/56* (2013.01); *C07D 487/04* (2013.01)
(58) Field of Classification Search
CPC .................................................. C07D 211/56
USPC .......................................................... 544/280
See application file for complete search history.

(56) References Cited

U.S. PATENT DOCUMENTS

| | | |
|---|---|---|
| 6,627,754 B2 | 9/2003 | Blumenkopf et al. |
| 6,956,041 B2 | 10/2005 | Blumenkopf et al. |
| 7,091,208 B2 | 8/2006 | Blumenkopf et al. |
| 7,265,221 B2 | 9/2007 | Blumenkopf et al. |
| 7,301,023 B2 | 11/2007 | Flanagan et al. |
| 7,432,370 B2 | 10/2008 | Wilcox et al. |
| 7,601,727 B2 | 10/2009 | Blumenkopf et al. |
| 7,842,699 B2 | 11/2010 | Blumenkopf et al. |
| 2001/0053782 A1 | 12/2001 | Blumenkopf et al. |
| 2003/0073719 A1 | 4/2003 | Wilcox et al. |
| 2004/0053947 A1 | 3/2004 | Blumenkopf et al. |
| 2004/0229923 A1 | 11/2004 | Wilcox et al. |
| 2005/0288313 A1 | 12/2005 | Blumenkopf et al. |
| 2006/0241131 A1 | 10/2006 | Blumenkopf et al. |
| 2007/0292430 A1 | 12/2007 | Blumenkopf et al. |
| 2010/0035903 A1 | 2/2010 | Blumenkopf et al. |
| 2012/0259115 A1 | 10/2012 | Gut Ruggeri et al. |
| 2015/0336961 A1 | 11/2015 | Bhirud et al. |
| 2016/0122354 A1 | 5/2016 | Thirumalai Rajan et al. |
| 2016/0297825 A1 | 10/2016 | Bonanomi et al. |
| 2019/0002407 A1 | 1/2019 | Pasto Aguila et al. |

FOREIGN PATENT DOCUMENTS

WO    2014/195978 A2    12/2014

OTHER PUBLICATIONS

Zhi et al., "An Efficient Method for Synthesis of Tofacitinib Citrate", Journal of Heterocyclic Chemistry, 2016, vol. 53, pp. 1259-1263.

*Primary Examiner* — Taofiq A Solola
(74) *Attorney, Agent, or Firm* — Vorys, Sater, Seymour and Pease LLP; Mih Suhn Koh

(57) ABSTRACT

Provided are a process for preparing (3R,4R)-1-benzyl-N, 4-dimethylpiperidin-3-amine or a salt thereof, which is an intermediate useful for the preparation of tofacitinib, an intermediate used in the process, i.e., isopropanol solvate of methyl ((3R,4R)-1-benzyl-4-methylpiperidin-3-yl)carbamate dibenzoyl-L-tartrate, an intermediate, having excellent stability, useful for the preparation of tofacitinib, i.e., (3R, 4R)-1-benzyl-N,4-dimethylpiperidin-3-amine acetate, and a process for preparing tofacitinib or a pharmaceutically acceptable salt thereof.

10 Claims, 10 Drawing Sheets

Initial6 months

Initial6 months

PROCESSES FOR PREPARING (3R,4R)-1-BENZYL-N,4-DIMETHYLPIPERIDIN-3-AMINE OR A SALT THEREOF AND PROCESSES FOR PREPARING TOFACITINIB USING THE SAME

TECHNICAL FIELD

The present invention relates to a novel process for preparing (3R,4R)-1-benzyl-N,4-dimethylpiperidin-3-amine or a salt thereof, which is an intermediate useful for the preparation of tofacitinib. The present invention also relates to a novel intermediate used in the process and a novel salt obtained by the process. In addition, the present invention relates to a process for preparing tofacitinib or a pharmaceutically acceptable salt thereof using the process.

BACKGROUND ART

Tofacitinib, whose chemical name is 3-[(3R,4R)-4-methyl-3-[methyl({7H-pyrrolo[2,3-d]pyrimidin-4-yl})amino]piperidin-1-yl]-3-oxopropanenitrile, is used in the citrate salt form of Formula 1 below. Tofacitinib is a Janus Kinase inhibitor and is useful for the treatment of rheumatoid arthritis, active psoriatic arthritis, and severe ulcerative colitis.

<Formula 1>

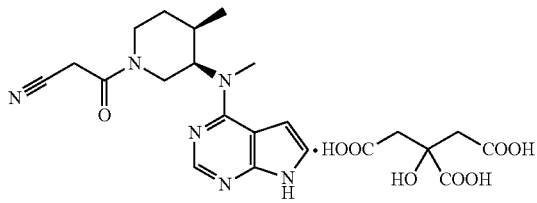

Processes for preparing tofacitinib or a citrate salt thereof have been disclosed in WO 2001/042246, WO 2002/096909, and the like. The processes comprise converting the intermediate (i.e., 1-benzyl-N,4-dimethylpiperidin-3-amine) to its stable form (i.e., its hydrochloride salt) and then performing the resolution thereof with a resolving agent such as L-tartaric acid or a derivative thereof or (+)-Phencyphos ((S)-(+)2-hydroxy-5,5-dimethyl-4-phenyl-1,3,2-dioxaphosphorinane-2-oxide). However, the step for converting racemic 1-benzyl-N,4-dimethylpiperidin-3-amine to its hydrochloride salt shows significantly low yield (62%). And also, since (+)-Phencyphos is a very expensive resolving reagent, there is a problem that the use thereof is not suitable for industrial mass production.

WO 2014/102826 discloses an improved process for preparing tofacitinib. WO 2014/102826 also discloses a process for preparing an optically active intermediate useful for the preparation of tofacitinib, the process of which comprises converting racemic methyl (4-methylpiperidin-3-yl)carbamate to racemic methyl (1-trityl-4-methylpiperidin-3-yl)carbamate, converting the racemic methyl (1-trityl-4-methylpiperidin-3-yl)carbamate to racemic 1-trityl-N,4-dimethylpiperidin-3-amine hydrochloride, and resolving the racemic 1-trityl-N,4-dimethylpiperidin-3-amine hydrochloride. However, the process disclosed in WO 2014/102826 has a disadvantage that the step for introducing a trityl group should be additionally carried out.

EP 3078665 discloses a process for preparing tofacitinib, comprising resolving the final intermediate of tofacitinib (i.e., N-methyl-N-(4-methylpiperidin-3-yl)-7H-pyrrolo[2,3-d]pyrimidin-4-amine) and then reacting cyanoacetic acid therewith. However, since the resolution is carried out almost at the final step in the tofacitinib synthesis, there is a problem that the manufacturing costs increase.

EP 3421455 discloses a process for preparing (3R,4R)-1-benzyl-N,4-dimethylpiperidin-3-amine hydrochloride, the process of which comprises performing asymmetric hydrogenation of racemic methyl (1-benzyl-4-methylpiperidin-3-yl)carbamate with a chiral catalyst such as rhodium catalyst having ferrocene ligands to prepare methyl ((3R,4R)-1-benzyl-4-methylpiperidin-3-yl)carbamate, and then performing a reduction and a reaction for converting to the hydrochloride salt thereof. However, the optical purity of the methyl ((3R,4R)-1-benzyl-4-methylpiperidin-3-yl)carbamate prepared by asymmetric hydrogenation is very low (82.3% ee). The optical purity of the prepared (3R,4R)-1-benzyl-N,4-dimethylpiperidin-3-amine hydrochloride is also very low (97.3% ee). And also, since the chiral catalyst used in the asymmetric hydrogenation is an expensive rhodium complex, there is a disadvantage that the manufacturing costs increase. In addition, there is a disadvantage that the yield of the step for preparing the hydrochloride salt is very low (60%).

DISCLOSURE OF INVENTION

Technical Problem

The present inventors have conducted various studies to develop an improved to process for preparing tofacitinib which is suitable for industrial mass production. Especially, the present inventors have conducted various studies to develop an improved process for preparing (3R,4R)-1-benzyl-N,4-dimethylpiperidin-3-amine or a salt thereof, an intermediate useful for the preparation of tofacitinib.

The present inventors have found that, when racemic methyl (1-benzyl-4-methylpiperidin-3-yl)carbamate is directly resolved in a certain solvent to prepare a certain solvate, followed by performing a step for the conversion to the free base thereof and a step for the reduction thereof, (3R,4R)-1-benzyl-N,4-dimethylpiperidin-3-amine or a salt thereof can be prepared in high yield and high optical purity. In addition, the present inventors have found that, when (3R,4R)-1-benzyl-N,4-dimethylpiperidin-3-amine is isolated in a certain salt form (i.e., in the form of acetate salt), the product thereof (i.e., (3R,4R)-1-benzyl-N,4-dimethylpiperidin-3-amine acetate) can be isolated in high optical purity and has excellent stability (such as storage stability, etc.).

Therefore, the present invention provides a novel process for preparing (3R,4R)-1-benzyl-N,4-dimethylpiperidin-3-amine or a salt thereof which is an intermediate useful for the preparation of tofacitinib.

And also, the present invention provides a novel intermediate used in the process.

And also, the present invention provides (3R,4R)-1-benzyl-N,4-dimethylpiperidin-3-amine acetate having excellent stability such as storage stability, etc.

And also, the present invention provides a process for preparing tofacitinib or a pharmaceutically acceptable salt thereof using the process.

Solution to Problem

According to an aspect of the present invention, there is provided a process for preparing (3R,4R)-1-benzyl-N,4-dimethylpiperidin-3-amine or a salt thereof, the process of which comprises:

(a) reacting racemic methyl (1-benzyl-4-methylpiperidin-3-yl)carbamate and dibenzoyl-L-tartaric acid by heating under reflux in a solvent selected from the group consisting of isopropanol, an aqueous solution of isopropanol, and a mixed solvent of isopropanol and an organic solvent, followed by cooling to prepare isopropanol solvate of methyl ((3R,4R)-1-benzyl-4-methylpiperidin-3-yl)carbamate dibenzoyl-L-tartrate; and (b) reacting the isopropanol solvate of methyl ((3R,4R)-1-benzyl-4-methylpiperidin-3-yl)carbamate dibenzoyl-L-tartrate prepared in Step (a) with a base to convert to methyl ((3R,4R)-1-benzyl-4-methylpiperidin-3-yl)carbamate, and then reducing the methyl ((3R,4R)-1-benzyl-4-methylpiperidin-3-yl)carbamate to prepare (3R,4R)-1-benzyl-N,4-dimethylpiperidin-3-amine.

In an embodiment, Step (b) may further comprises reacting the (3R,4R)-1-benzyl-N,4-dimethylpiperidin-3-amine with acetic acid to prepare (3R,4R)-1-benzyl-N,4-dimethylpiperidin-3-amine acetate [i.e., Step (c)].

In accordance with another aspect of the present invention, there is provided isopropanol solvate of methyl ((3R,4R)-1-benzyl-4-methylpiperidin-3-yl)carbamate dibenzoyl-L-tartrate.

In accordance with still another aspect of the present invention, there is provided (3R,4R)-1-benzyl-N,4-dimethylpiperidin-3-amine acetate.

In accordance with still another aspect of the present invention, there is provided a process for preparing tofacitinib or a pharmaceutically acceptable salt thereof, the process of which comprises:

(i) preparing (3R,4R)-1-benzyl-N,4-dimethylpiperidin-3-amine or a salt thereof according to the above process;

(ii) reacting the (3R,4R)-1-benzyl-N,4-dimethylpiperidin-3-amine or a salt thereof with 2,4-dichloro-7H-pyrrolo[2,3-d]pyrimidine to prepare (3R,4R)-(1-benzyl-4-methylpiperidin-3-yl)-2-chloro-N-methyl-(7H-pyrrolo[2,3-d]pyrimidin-4-yl)-amine;

(iii) performing debenzylation of the (3R,4R)-(1-benzyl-4-methylpiperidin-3-yl)-2-chloro-N-methyl-(7H-pyrrolo[2,3-d]pyrimidin-4-yl)-amine to prepare (3R,4R)-(4-methylpiperidin-3-yl)-N-methyl-(7H-pyrrolo[2,3-d]pyrimidin-4-yl)-amine, and (iv) reacting the (3R,4R)-(4-methylpiperidin-3-yl)-N-methyl-(7H-pyrrolo[2,3-d]pyrimidin-4-yl)-amine with ethyl cyanoacetate to prepare tofacitinib.

Advantageous Effects of Invention

The process according to the present invention can provides (3R,4R)-1-benzyl-N,4-dimethylpiperidin-3-amine or a salt thereof in high yield and high optical purity. And also, a certain salt obtained by the present invention, i.e., (3R,4R)-1-benzyl-N,4-dimethylpiperidin-3-amine acetate has excellent stability (such as storage stability, etc.) and thus can be usefully applied as an intermediate for the preparation of tofacitinib. Especially, when (3R,4R)-1-benzyl-N,4-dimethylpiperidin-3-amine is isolated in the form of acetate salt, the optical purity of methyl ((3R,4R)-1-benzyl-4-methylpiperidin-3-yl)carbamate dibenzoyl-L-tartrate can be increased, for example from 95.2% of chiral purity to 99.8% of chiral purity.

BEST MODE FOR CARRYING OUT THE INVENTION

Figure 1:
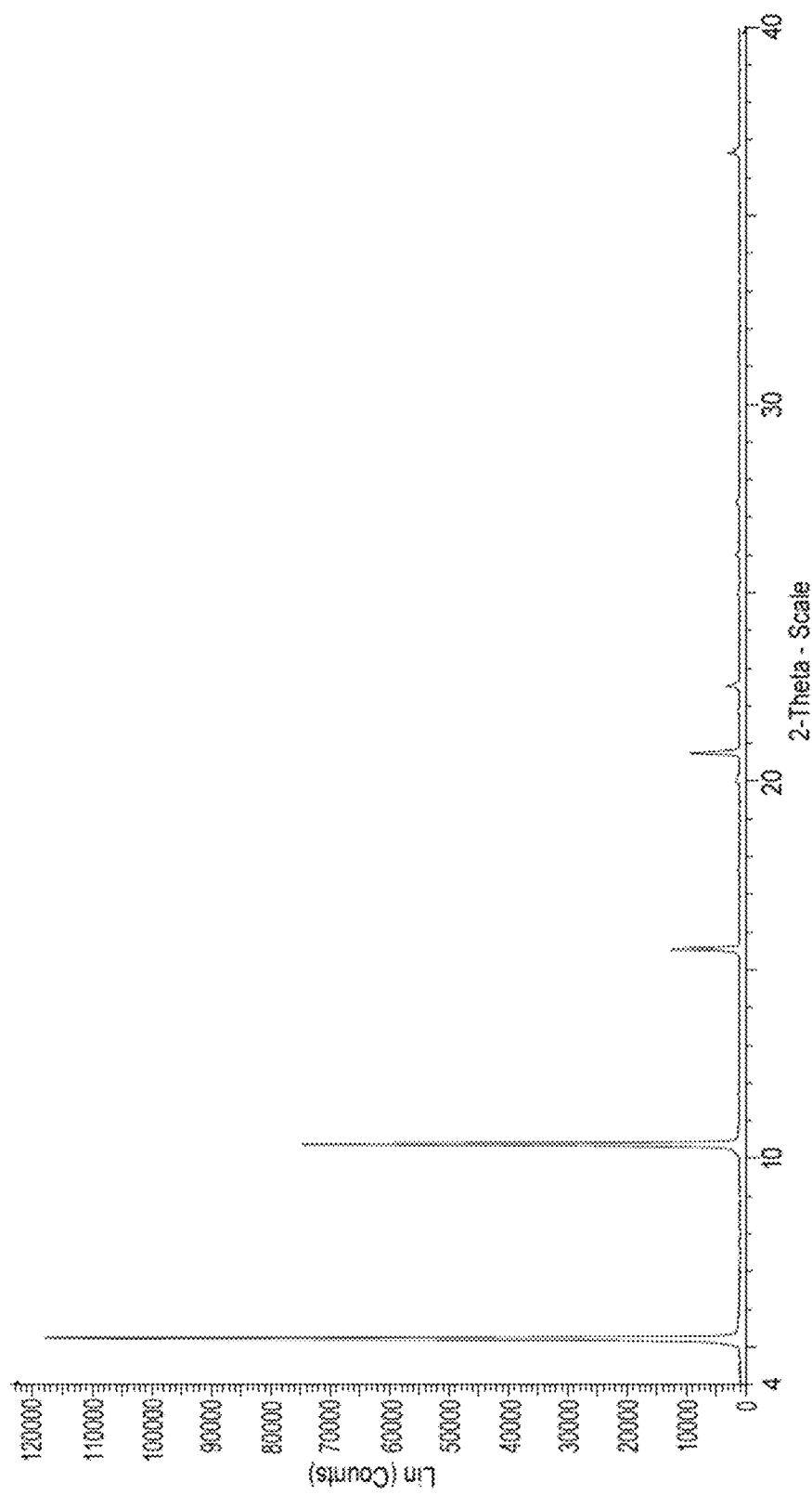
FIG. 1 shows the PXRD spectrum of isopropanol solvate of methyl ((3R,4R)-1-benzyl-4-methylpiperidin-3-yl)carbamate dibenzoyl-L-tartrate prepared in Example 2.

The present invention provides a novel process for preparing (3R,4R)-1-benzyl-N,4-dimethylpiperidin-3-amine or a salt thereof which is an intermediate useful for the preparation of tofacitinib. Specifically, the present invention provides a process for preparing (3R,4R)-1-benzyl-N,4-dimethylpiperidin-3-amine or a salt thereof, the process of which comprises:

(a) reacting racemic methyl (1-benzyl-4-methylpiperidin-3-yl)carbamate and dibenzoyl-L-tartaric acid by heating under reflux in a solvent selected from the group consisting of isopropanol, an aqueous solution of isopropanol, and a mixed solvent of isopropanol and an organic solvent, followed by cooling to prepare isopropanol solvate of methyl ((3R,4R)-1-benzyl-4-methylpiperidin-3-yl)carbamate dibenzoyl-L-tartrate; and (b) reacting the isopropanol solvate of methyl ((3R,4R)-1-benzyl-4-methylpiperidin-3-yl)carbamate dibenzoyl- L-tartrate prepared in Step (a) with a base to convert to methyl ((3R,4R)-1-benzyl-4-methylpiperidin-3-yl)carbamate, and then reducing the methyl ((3R,4R)-1-benzyl-4-methylpiperidin-3-yl)carbamate to prepare (3R,4R)-1-benzyl-N,4-dimethylpiperidin-3-amine.

In the process of the present invention, the racemic methyl (1-benzyl-4-methylpiperidin-3-yl)carbamate is a known compound and therefore commercially available. If necessary, an acid addition salt such as racemic methyl (1-benzyl-4-methylpiperidin-3-yl)carbamate hydrochloride is treated with a base such as potassium carbonate for converting to racemic methyl (1-benzyl-4-methylpiperidin-3-yl)carbamate, which may be used in the process.

The reaction of Step (a) is carried out in a solvent selected from the group consisting of isopropanol, an aqueous solution of isopropanol, and a mixed solvent of isopropanol and an organic solvent. The mixed solvent of isopropanol and an organic solvent may be a mixed solvent of isopropanol and an organic solvent selected from the group consisting of methanol, ethanol, n-propanol, acetone, methylethylketone, methyl acetate, ethyl acetate, tetrahydrofuran, 2-methyltetrahydrofuran and acetonitrile. Preferably, the reaction of Step (a) may be carried out in isopropanol, an aqueous solution of isopropanol, a mixed solvent of isopropanol and methanol, a mixed solvent of isopropanol and ethanol, or a mixed solvent of isopropanol and n-propanol. In the aqueous solution of isopropanol and the mixed solvent of isopropanol and an organic solvent, a volumetric ratio of isopropanol: water or the organic solvent may be 60:1 to 30:1.

In Step (a), dibenzoyl-L-tartaric acid used as a resolving agent may be used in a ratio ranging from 0.5 to 2.0 equivalents, preferably 0.7 to 1.1 equivalents, based on 1 equivalent of racemic methyl (1-benzyl-4-methylpiperidin-3-yl)carbamate. Dibenzoyl-L-tartaric acid may be directly added to a solution of racemic methyl (1-benzyl-4-methylpiperidin-3-yl)carbamate. Alternatively, dibenzoyl-L-tartaric acid may be added, in the form of a solution containing dibenzoyl-L-tartaric acid, to a solution of racemic methyl (1-benzyl-4-methylpiperidin-3-yl)carbamate. The reaction of racemic methyl (1-benzyl-4-methylpiperidin-3-yl)carbamate with dibenzoyl-L-tartaric acid is carried out by heating under reflux. The heating under reflux may be carried out e.g., at a temperature ranging from 55 to 100° C., although it is different depending on the solvent used. The cooling after the heating under reflux may be carried out to a temperature ranging from 0 to 55° C. The cooling results in precipitation of the stereospecific enantiomer. The cooling/precipitation process may be carried out, for example, for 1 to 24 hours, preferably for 2 to 5 hours, more preferably for about 3 hours, but not limited thereto. The resulting precipitate may be isolated through processes such as filtration, washing and drying. For example, the drying may be carried out at 30 to 60° C., preferably at 40 to 50° C., but not limited thereto.

It has been found by the present invention that the product obtained in Step (a) is in the form of isopropanol solvate of methyl ((3R,4R)-1-benzyl-4-methylpiperidin-3-yl)carbamate dibenzoyl-L-tartrate, which is represented by the following Formula 3. That is, the product obtained in Step (a) is in the solvate form in which methyl ((3R,4R)-1-benzyl-4-methylpiperidin-3-yl)carbamate, dibenzoyl-L-tartaric acid, and isopropanol are combined in the equivalent ratio of 1:1:1. The isopropanol solvate of methyl ((3R,4R)-1-benzyl-4-methylpiperidin-3-yl)carbamate dibenzoyl-L-tartrate may be subsequently reacted with a base such as carbonate or hydroxide, etc. to convert a free base form, which allows the next reaction step to be carried out efficiently. Since the process of the present invention proceeds via isopropanol solvate of methyl ((3R,4R)-1-benzyl-4-methylpiperidin-3-yl)carbamate dibenzoyl-L-tartrate, the chiral resolution is carried out at the more previous step in comparison with the known methods, which makes it possible to lower the manufacturing costs and to provide the product having high optical purity.

<Formula 3>

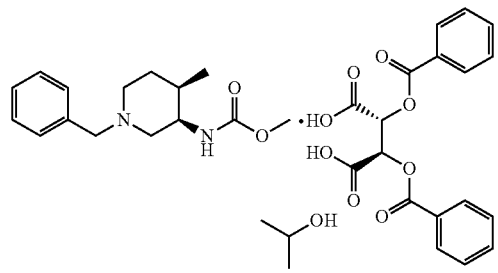

It has been found by the present invention that recrystallization of the isopropanol solvate of methyl ((3R,4R)-1-benzyl-4-methylpiperidin-3-yl)carbamate dibenzoyl-L-tartrate prepared in Step (a) with a certain solvent can increase the chiral purity thereof to 99% or more, more preferably to 99.5% or more, still more preferably to 99.8% or more, especially more preferably to 99.9% or more. Therefore, Step (a) may further comprise a recrystallizing step. Specifically, Step (a) may further comprise recrystallizing the resulting isopropanol solvate of methyl ((3R,4R)-1-benzyl-4-methylpiperidin-3-yl)carbamate dibenzoyl-L-tartrate in a mixed solvent of isopropanol and methanol or a mixed solvent of isopropanol and ethanol. The recrystallizing may be carried out for example, by heating under reflux a mixture of isopropanol solvate of methyl ((3R,4R)-1-benzyl-4-methylpiperidin-3-yl)carbamate dibenzoyl-L-tartrate and a mixed solvent of isopropanol and methanol or a mixed solvent of isopropanol and ethanol, followed by cooling to a temperature ranging from 5 to 15° C. for the precipitation thereof. The resulting precipitate may be isolated through processes such as filtration, washing and drying. For example, the drying may be carried out at 30 to 60° C., preferably at 40 to 50° C., but not limited thereto.

The process of the present invention includes reacting the isopropanol solvate of methyl ((3R,4R)-1-benzyl-4-methylpiperidin-3-yl)carbamate dibenzoyl-L-tartrate prepared in the above with a base to convert to methyl ((3R,4R)-1-benzyl-4-methylpiperidin-3-yl)carbamate, and then reducing the methyl ((3R,4R)-1-benzyl-4-methylpiperidin-3-yl)carbamate to prepare (3R,4R)-1-benzyl-N,4-dimethylpiperidin-3-amine [i.e., Step (b)].

The base used for converting to methyl ((3R,4R)-1-benzyl-4-methylpiperidin-3-yl)carbamate (i.e., for converting to a free base form) may be a conventional inorganic base, such as potassium carbonate, potassium hydrogen carbonate, sodium hydrogen carbonate, sodium carbonate, sodium hydroxide, potassium hydroxide, preferably potassium carbonate. The base may be used in a ratio ranging from 1.0 to 5.0 equivalents, based on 1 equivalent of isopropanol solvate of methyl ((3R,4R)-1-benzyl-4-methylpiperidin-3-yl)carbamate dibenzoyl-L-tartrate, but not limited thereto. The reaction of isopropanol solvate of methyl ((3R,4R)-1-benzyl-4-methylpiperidin-3-yl)carbamate dibenzoyl-L-tartrate with a base may be carried out in a conventional organic solvent such as methyl t-butyl ether.

The reducing agent for forming (3R,4R)-1-benzyl-N,4-dimethylpiperidin-3-amine may be for example lithium aluminium hydride, lithium bis(2-methoxyethoxy)aluminum hydride, sodium hydride and the like, preferably lithium aluminium hydride. The reducing agent may be used in a ratio ranging from 1.0 to 5.0 equivalents, based on 1 equivalent of methyl ((3R,4R)-1-benzyl-4-methylpiperidin-3-yl)carbamate, but not limited thereto. The reduction may be carried out in a conventional organic solvent such as tetrahydrofuran.

It has been found by the present invention that, when (3R,4R)-1-benzyl-N,4-dimethylpiperidin-3-amine is converted to a certain salt form (i.e., to the acetate salt form), the resulting (3R,4R)-1-benzyl-N,4-dimethylpiperidin-3-amine acetate can be isolated in high optical purity (99% ee or more) and has excellent stability (such as storage stability, etc.). Therefore, the process of the present invention may further comprise converting (3R,4R)-1-benzyl-N,4-dimethylpiperidin-3-amine to an acetate salt thereof. Specifically, the process of the present invention may further comprise reacting the (3R,4R)-1-benzyl-N,4-dimethylpiperidin-3-amine with acetic acid to prepare (3R,4R)-1-benzyl-N,4-dimethylpiperidin-3-amine acetate [Step (c)].

Acetic acid may be used in a ratio ranging from 0.8 to 1.5 equivalents, preferably from 0.9 to 1.1 equivalents, based on 1 equivalent of (3R,4R)-1-benzyl-N,4-dimethylpiperidin-3-amine. The reaction of (3R,4R)-1-benzyl-N,4-dimethylpiperidin-3-amine with acetic acid may be carried out in a solvent selected from the group consisting of methanol, ethanol, isopropanol, n-propanol, acetone, methylethylketone, methyl acetate, ethyl acetate, isopropyl acetate, tetrahydrofuran, 2-methyltetrahydrofuran, acetonitrile, and a mixed solvent thereof. Preferably, the reaction may be carried out in acetone, methylethylketone, ethyl acetate, isopropyl acetate, or a mixed solvent thereof. And also, the reaction may be carried out at a temperature ranging from 30 to 50° C., preferably from 30 to 40° C. for 1-3 hours. The product may be isolated through processes such as cooling, filtration of the precipitate, washing and drying. For example, the cooling may be carried out at −5 to 10° C., preferably at 0 to 5° C.; and the drying may be carried out at 20 to 50° C., preferably at 35 to 45° C., but not limited thereto.

The present invention also includes, within its scope, the novel solvate of Formula 3 used as an intermediate in the process, i.e., isopropanol solvate of methyl ((3R,4R)-1-benzyl-4-methylpiperidin-3-yl)carbamate dibenzoyl-L-tartrate.

The present invention also includes, within its scope, the novel stereoisomer intermediate useful for the preparation of tofacitinib, i.e., (3R,4R)-1-benzyl-N,4-dimethylpiperidin-3-amine acetate of Formula 4.

<Formula 4>

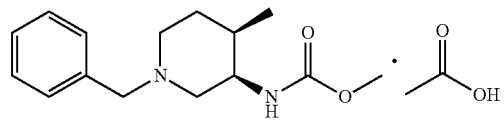

The present invention also includes, within its scope, a process for preparing tofacitinib or a pharmaceutically acceptable salt thereof, comprising converting the (3R,4R)-1-benzyl-N,4-dimethylpiperidin-3-amine or a salt thereof (preferably an acetate salt) prepared according to the above process to tofacitinib. Specifically, the present invention provides a process for preparing tofacitinib or a pharmaceutically acceptable salt thereof, the process of which comprises:

(i) preparing (3R,4R)-1-benzyl-N,4-dimethylpiperidin-3-amine or a salt thereof according to the process according to the above process;

(ii) reacting the (3R,4R)-1-benzyl-N,4-dimethylpiperidin-3-amine or a salt thereof with 2,4-dichloro-7H-pyrrolo[2,3-d]pyrimidine to prepare (3R,4R)-(1-benzyl-4-methylpiperidin-3-yl)-2-chloro-N-methyl-(7H-pyrrolo[2,3-d]pyrimidin-4-yl)-amine;

(iii) performing debenzylation of the (3R,4R)-(1-benzyl-4-methylpiperidin-3-yl)-2-chloro-N-methyl-(7H-pyrrolo[2,3-d]pyrimidin-4-yl)-amine to prepare (3R,4R)-(4-methylpiperidin-3-yl)-N-methyl-(7H-pyrrolo[2,3-d]pyrimidin-4-yl)-amine, and (iv) reacting the (3R,4R)-(4-methylpiperidin-3-yl)-N-methyl-(7H-pyrrolo[2,3-d]pyrimidin-4-yl)-amine with ethyl cyanoacetate to prepare tofacitinib.

In the process, the salt of (3R,4R)-1-benzyl-N,4-dimethylpiperidin-3-amine may be (3R,4R)-1-benzyl-N,4-dimethylpiperidin-3-amine acetate.

Steps (ii) to (iv) may be carried out according to known methods (for example, the methods disclosed in WO2002/096909, *J. Heterocyclic. Chem*, 53, 1259(2016), *Org. Process Res. Dev.* 2014, 18, 1714, and the like), except for using (3R,4R)-1-benzyl-N,4-dimethylpiperidin-3-amine or an acetate salt thereof prepared according to the present invention.

The overall reaction scheme of the process of the present invention is represented as the following Reaction Scheme 1.

<Reaction Scheme 1>

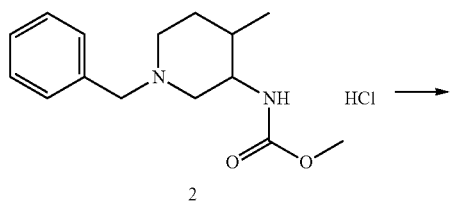

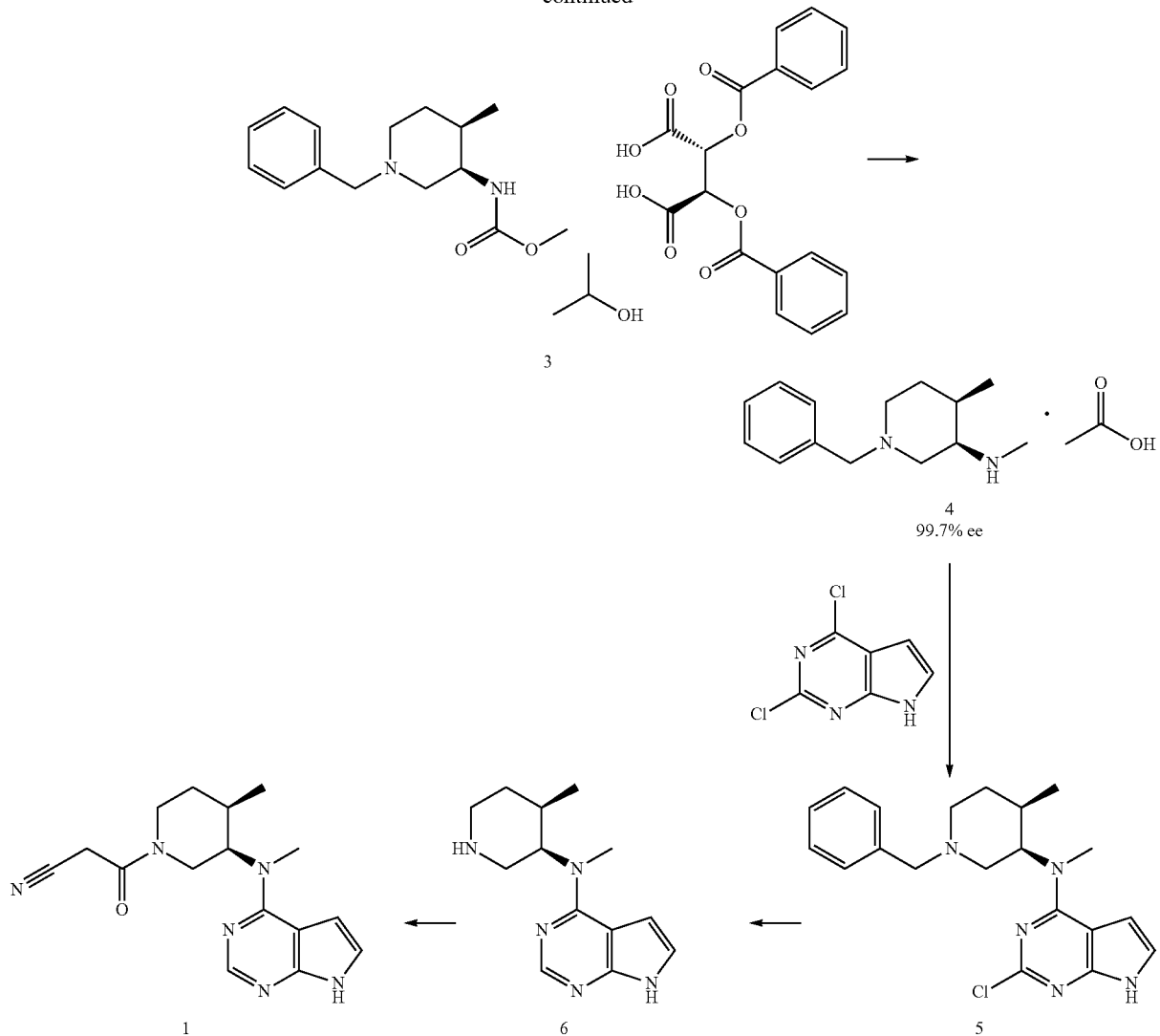

The present invention will be described in further detail with reference to the following examples. These examples are for illustrative purposes only and are not intended to limit the scope of the present invention.

The powder X-ray diffraction (PXRD) spectrum was measured with the Bruker D8 advance X-ray powder diffractometer (X-ray source: CuKα, tube voltage: 40 kV, tube current: 40 mA, divergence slit: 0.3° and scattering slit: 0.3°). The FT-IR spectrum was measured with the Agilent Cary 630 FT-IR spectrometer, where the sample was brought into close contact with the surface of the ATR prism and then the reflectance spectrum thereof was measured at the wave number ranging from 4000 to 650 cm$^{-1}$. Mass measurement was performed on the Waters e2695 QDa mass spectrometer (Waters e2695 separation modules with QDa detector) (capillary voltage: 0.8 kV, probe temperature: 600° C., cone voltage: 10V, source: electrospray, analysis mode: positive mode, and scan range: 50 to 1000 Da). Melting point (M.P) measurement was carried out with the Mettler Toledo MP80 melting point system (start temperature: 120° C., end temperature: 200° C., and heating rate: 1° C./min). Optical rotation measurement was carried out with the Jasco P-2000 series polarimeter (wavelength: 589 nm, path length: 100 mm, 1 g/100 mL in CHCl$_3$ at 20° C.). Differential scanning calorimetry (DSC) measurement was carried out with the Mettler Toledo DSC 1 STAR Differential Scanning calorimeter (sample vessel: sealed aluminum pan, 99% nitrogen condition, start temperature: 30° C., end temperature: 300° C., and heating rate: 10° C./min). Nuclear magnetic resonance (NMR) spectrum analysis was carried out with the Bruker 400 MHz spectrometer and chemical shifts thereof were analyzed in ppm.

Example 1: Preparation of Isopropanol Solvate of Methyl ((3R,4R)-1-benzyl-4-methylpiperidin-3-yl)carbamate Dibenzoyl-L-Tartrate A mixture of racemic methyl (1-benzyl-4-methylpiperidin-3-yl)carbamate hydrochloride (840 g), methyl t-butyl ether (8.4 L), and a potassium carbonate solution (427 g in 3.4 L of purified water) was stirred at room temperature for about 15 minutes. The organic layer was separated and then concentrated under reduced pressure. Isopropanol (1.7 L) was added to the concentrate and the resulting mixture was additionally concentrated under reduced pressure. Isopropanol (3.4 L) was added to the concentrate and the resulting mixture was stirred for about 15 minutes. A solution of dibenzoyl-L-tartaric acid (1.0 kg) in isopropanol (10.0 L) was slowly added to the above solution of racemic methyl (1-benzyl-4-methylpiperidin-3-yl)carbamate in isopropanol. The reaction mixture was heated under reflux for about 3 hours, cooled to about 50° C., and then stirred at 50±5° C. for about 3 hours. The product was filtered and then washed with isopropanol (0.8 L). The resulting wet cake was dried under vacuum at about 45° C. to obtain 897.5 g of isopropanol solvate of methyl ((3R,4R)-1-benzyl-4-methylpiperidin-3-yl)carbamate dibenzoyl-L-tartrate. (Yield: 46.9%)

Chiral purity: 98.0%

$^1$H-NMR (400 MHz, DMSO-$d_6$) δ 8.0 (m, 4H), 7.69 (m, 2H), 7.55 (m, 4H), 7.30-7.38 (m, 5H), 7.09 (m, 1H), 5.79 (d, 2H), 3.74-3.89 (m, 4H), 3.46 (s, 3H), 2.81-2.91 (m, 2H), 2.62 (m, 2H), 1.73 (b, 1H), 1.41-1.53 (m, 2H), 1.03 (d, 6H), 0.73 (d, 3H)

Example 2: Purification of Isopropanol Solvate of Methyl ((3R,4R)-1-benzyl-4-methylpiperidin-3-yl)carbamate Dibenzoyl-L-Tartrate A mixture of isopropanol solvate of methyl ((3R,4R)-1-benzyl-4-methylpiperidin-3-yl)carbamate dibenzoyl-L-tartrate (100 g, chiral purity: 98.0%) prepared in Example 1, isopropanol (2.7 L) and methanol (0.3 L) was heated under reflux for about 3 hours, cooled to about 10° C., and then stirred at 10±5° C. for about 3 hours. The product was filtered and then washed with a mixed solvent of isopropanol and methanol (0.2 L, 27:3 (v/v)). The resulting wet cake was dried under vacuum at about 45° C. to obtain 94.2 g of isopropanol solvate of methyl ((3R,4R)-1-benzyl-4-methylpiperidin-3-yl)carbamate dibenzoyl-L-tartrate. (Yield: 94.2%)

Chiral purity: 99.90%

M.P 134.5-136.5° C.

MS m/z 263 (M$^+$+H)

$^1$H-NMR (400 MHz, DMSO-$d_6$) δ 8.0 (m, 4H), 7.69 (m, 2H), 7.55 (m, 4H), 7.30-7.38 (m, 5H), 7.09 (m, 1H), 5.79 (d, 2H), 3.74-3.89 (m, 4H), 3.46 (s, 3H), 2.81-2.91 (m, 2H), 2.62 (m, 2H), 1.73 (b, 1H), 1.41-1.53 (m, 2H), 1.03 (d, 6H), 0.73 (d, 3H).

Optical rotation: 8.93°~10.02°

The PXRD spectrum of the obtained isopropanol solvate of methyl ((3R,4R)-1-benzyl-4-methylpiperidin-3-yl)carbamate dibenzoyl-L-tartrate is shown in FIG. 1. As shown FIG. 1, diffraction peaks exist where the 2θ angles are 5.18±0.2°, 10.34±0.2°, 15.52±0.2°, 20.73±0.2°, 22.53±0.2°, and 36.66±0.2°.

Figure 2:
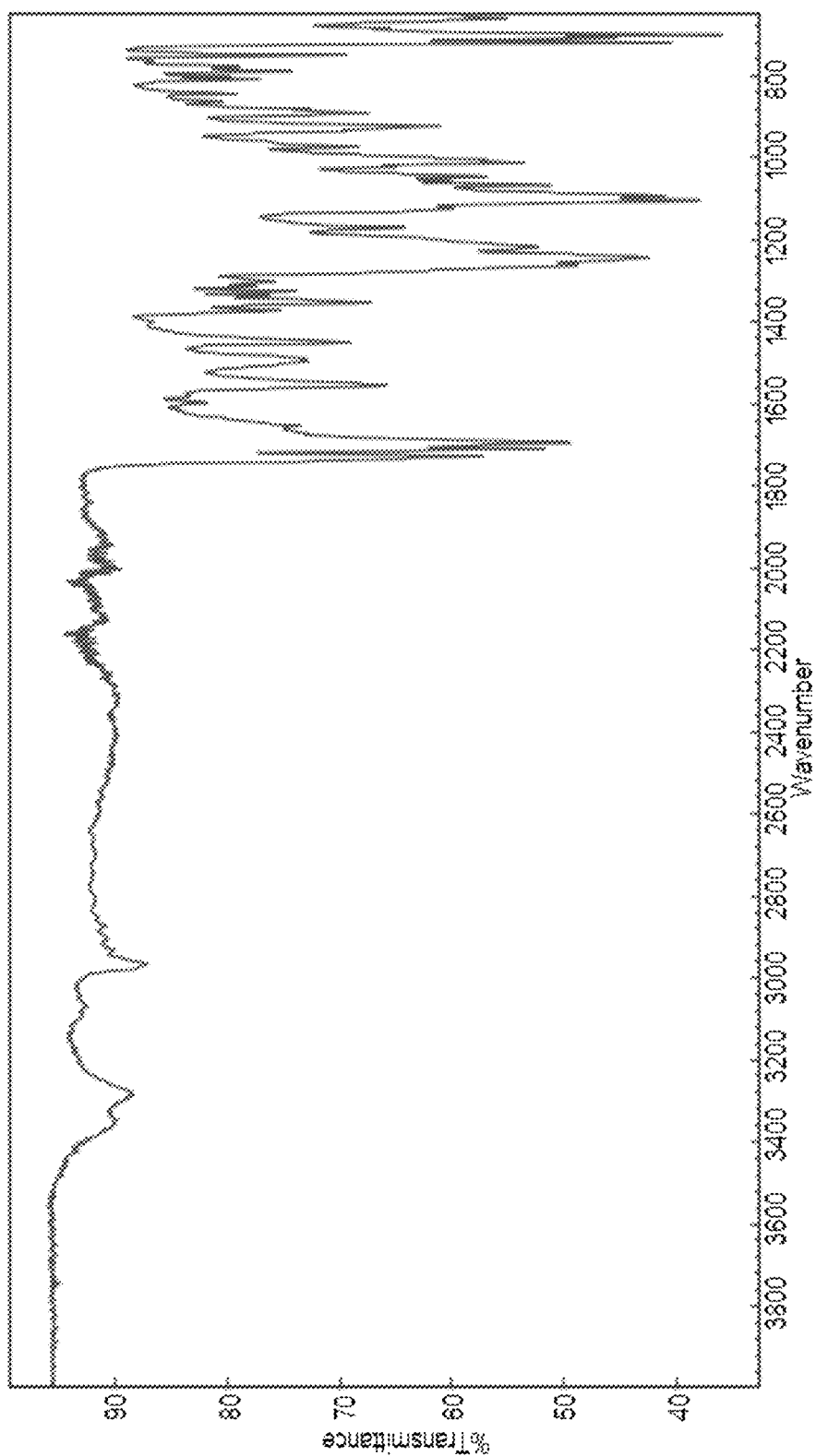
FIG. 2 shows the FT-IR spectrum of isopropanol solvate of methyl ((3R,4R)-1-benzyl-4-methylpiperidin-3-yl)carbamate dibenzoyl-L-tartrate prepared in Example 2.

And also, the FT-IR spectrum of the obtained isopropanol solvate of methyl ((3R,4R)-1-benzyl-4-methylpiperidin-3-yl)carbamate dibenzoyl-L-tartrate is shown in FIG. 2. As shown FIG. 2, infrared absorption frequencies (cm$^{-1}$) are 3287, 2970, 1732, 1713, 1697, 1557, 1498, 1450, 1373, 1354, 1307, 1265, 1247, 1221, 1172, 1107, 1070, 1050, 1015, 976, 927, 895, 847, 811, 752, 723, 705, 664, 649, 592, 563, 515, and 497.

Example 3: Purification of Isopropanol Solvate of Methyl ((3R,4R)-1-benzyl-4-methylpiperidin-3-yl)carbamate Dibenzoyl-L-Tartrate A mixture of isopropanol solvate of methyl ((3R,4R)-1-benzyl-4-methylpiperidin-3-yl)carbamate dibenzoyl-L-tartrate (100 g, chiral purity: 98.0%) prepared in Example 1, isopropanol (2.7 L) and absolute ethanol (0.3 L) was heated under reflux for about 3 hours, cooled to about 10° C., and then stirred at 10±5° C. for about 3 hours. The product was filtered and then washed with a mixed solvent of isopropanol and absolute ethanol (0.2 L, 27:3 (v/v)). The resulting wet cake was dried under vacuum at about 45° C. to obtain 95.4 g of isopropanol solvate of methyl ((3R,4R)-1-benzyl-4-methylpiperidin-3-yl)carbamate dibenzoyl-L-tartrate. (Yield: 95.4%)

Chiral purity: 99.86%

$^1$H-NMR (400 MHz, DMSO-$d_6$) δ 8.0 (m, 4H), 7.69 (m, 2H), 7.55 (m, 4H), 7.30-7.38 (m, 5H), 7.09 (m, 1H), 5.79 (d, 2H), 3.74-3.89 (m, 4H), 3.46 (s, 3H), 2.81-2.91 (m, 2H), 2.62 (m, 2H), 1.73 (b, 1H), 1.41-1.53 (m, 2H), 1.03 (d, 6H), 0.73 (d, 3H)

Example 4: Preparation of Isopropanol Solvate of Methyl ((3R,4R)-1-benzyl-4-methylpiperidin-3-yl)carbamate Dibenzoyl-L-Tartrate A mixture of racemic methyl (1-benzyl-4-methylpiperidin-3-yl)carbamate hydrochloride (10 g), methyl t-butyl ether (100 mL), and a potassium carbonate solution (5 g in 40 mL of purified water) was stirred at room temperature for about 15 minutes. The organic layer was separated and then concentrated under reduced pressure. Isopropanol (20 mL) was added to the concentrate and the resulting mixture was additionally concentrated under reduced pressure. Isopropanol (285 mL) and purified water (15 mL) were added to the concentrate and the resulting mixture was stirred for about 15 minutes. Dibenzoyl-L-tartaric acid (12.0 g) was added to the above solution. The reaction mixture was heated under reflux for 1 hour, cooled to about 50° C., and then stirred at 50±5° C. for about 3 hours. The product was filtered and then washed with isopropanol (10 mL). The resulting wet cake was dried under vacuum at about 45° C. to obtain 8.3 g of isopropanol solvate of methyl ((3R,4R)-1-benzyl-4-methylpiperidin-3-yl)carbamate dibenzoyl-L-tartrate. (Yield: 36.5%)

Chiral purity: 96.54%

$^1$H-NMR (400 MHz, DMSO-$d_6$) δ 8.0 (m, 4H), 7.69 (m, 2H), 7.55 (m, 4H), 7.30-7.38 (m, 5H), 7.09 (m, 1H), 5.79 (d, 2H), 3.74-3.89 (m, 4H), 3.46 (s, 3H), 2.81-2.91 (m, 2H), 2.62 (m, 2H), 1.73 (b, 1H), 1.41-1.53 (m, 2H), 1.03 (d, 6H), 0.73 (d, 3H)

Example 5: Preparation of Isopropanol Solvate of Methyl ((3R,4R)-1-benzyl-4-methylpiperidin-3-yl)carbamate Dibenzoyl-L-Tartrate A mixture of racemic methyl (1-benzyl-4-methylpiperidin-3-yl)carbamate hydrochloride (3.0 kg), methyl t-butyl ether (30.0 L), and a potassium carbonate solution (1.5 kg in 12 L of purified water) was stirred at room temperature for about 15 minutes. The organic layer was separated and then concentrated under reduced pressure. Isopropanol (6.0 L) was added to the concentrate and the resulting mixture was additionally concentrated under reduced pressure. Isopropanol (6.0 L) was added to the concentrate and the resulting mixture was stirred for about 15 minutes. A solution of dibenzoyl-L-tartaric acid (2.5 kg) in isopropanol (30.0 L) was slowly added to the above solution of racemic methyl (1-benzyl-4-methylpiperidin-3-yl)carbamate in isopropanol. The reaction mixture was heated under reflux for 3 hours, cooled to about 50° C., and then stirred at 50±5° C. for about 3 hours. The product was filtered and then washed with isopropanol (3.0 L). A mixture of the resulting wet cake, isopropanol (85.4 L), and methanol (10.2 L) was heated under reflux for 3 hours, cooled to about 10° C., and then stirred at 10±5° C. for about 3 hours. The product was filtered and then washed with mixed solvent of isopropanol and methanol (6.8 L, 27:3 (v/v)). The resulting wet cake was dried under vacuum at about 45° C. to obtain 3.0 kg of isopropanol solvate of methyl ((3R,4R)-1-benzyl-4-methylpiperidin-3-yl)carbamate dibenzoyl-L-tartrate. (Yield: 43.9%)

Chiral purity: 99.93%

$^1$H-NMR (400 MHz, DMSO-$d_6$) δ 8.0 (m, 4H), 7.69 (m, 2H), 7.55 (m, 4H), 7.30-7.38 (m, 5H), 7.09 (m, 1H), 5.79 (d, 2H), 3.74-3.89 (m, 4H), 3.46 (s, 3H), 2.81-2.91 (m, 2H), 2.62 (m, 2H), 1.73 (b, 1H), 1.41-1.53 (m, 2H), 1.03 (d, 6H), 0.73 (d, 3H)

Example 6: Preparation of (3R,4R)-1-benzyl-N,4-dimethylpiperidin-3-amine Acetate A mixture of isopropanol solvate of methyl ((3R,4R)-1-benzyl-4-methylpiperidin-3-yl)carbamate dibenzoyl-L-tartrate (1:1:1, chiral purity: 99.93%) (2.5 kg) and methyl t-butyl ether (25.0 L) was cooled to 10° C. or less and then a 10% potassium carbonate solution (15.0 L) was added thereto. The reaction mixture was stirred for about 30 minutes. The organic layer was separated, washed with purified water (2.5 L), and then concentrated under reduced pressure. Tetrahydrofuran (3.5 L) was added to the concentrate and the resulting mixture was additionally concentrated under reduced pressure. Tetrahydrofuran (16.3 L) was added to the concentrate and the resulting mixture was stirred for about 15 minutes. Lithium aluminium hydride (181.6 g) was added to the solution in three portions. The reaction mixture was heated under reflux for 3 hours, cooled to −10∼−5° C. An aqueous tetrahydrofuran solution (1.8 L, THF:purified water=5:2, (v/v)) was slowly added thereto, while maintaining the internal temperate to 0° C. or less. After the temperature of the reaction mixture was raised to room temperature, the reaction mixture was stirred for about 30 minutes and then filtered. The wet cake was washed with tetrahydrofuran (5.0 L). The filtrate and the rinsed solution were combined and then the resulting mixture was concentrated under reduced pressure. Isopropyl acetate (5.0 L) was added to the concentrate and the resulting mixture was additionally concentrated under reduced pressure. Methylethylketone (12.5 L) was added to the concentrate and the resulting mixture was stirred at 35±5° C. for about 15 minutes. Acetic acid (220.5 g) was added to the resulting solution. The reaction mixture was stirred for about 30 minutes, cooled to about 5° C., and then stirred at 0-5° C. for about 1 hour. The product was filtered and then washed with cold methylethylketone (2.5 L). The resulting wet cake was dried under vacuum at about 40° C. to obtain 889.3 g of (3R,4R)-1-benzyl-N,4-dimethylpiperidin-3-amine acetate. (Yield: 87.0%)

Chemical purity: 99.99%
Chiral purity: 100%
M.P 116.5~118.5° C.
MS m/z 219 (M$^+$+H)

$^1$H-NMR (400 MHz, DMSO-$d_6$) δ 8.0 (m, 4H), 7.31 (m, 4H), 7.25 (m, 2H), 3.61 (d, 1H), 3.40 (d, 1H), 2.76 (b, 3H), 2.35 (s, 3H), 2.21 (b, 2H), 1.99 (s, 3H), 1.83 (b, 1H), 1.50 (b, 2H), 1.04 (d, 3H)

Optical rotation 26.9° ~28.2°

Figure 3:
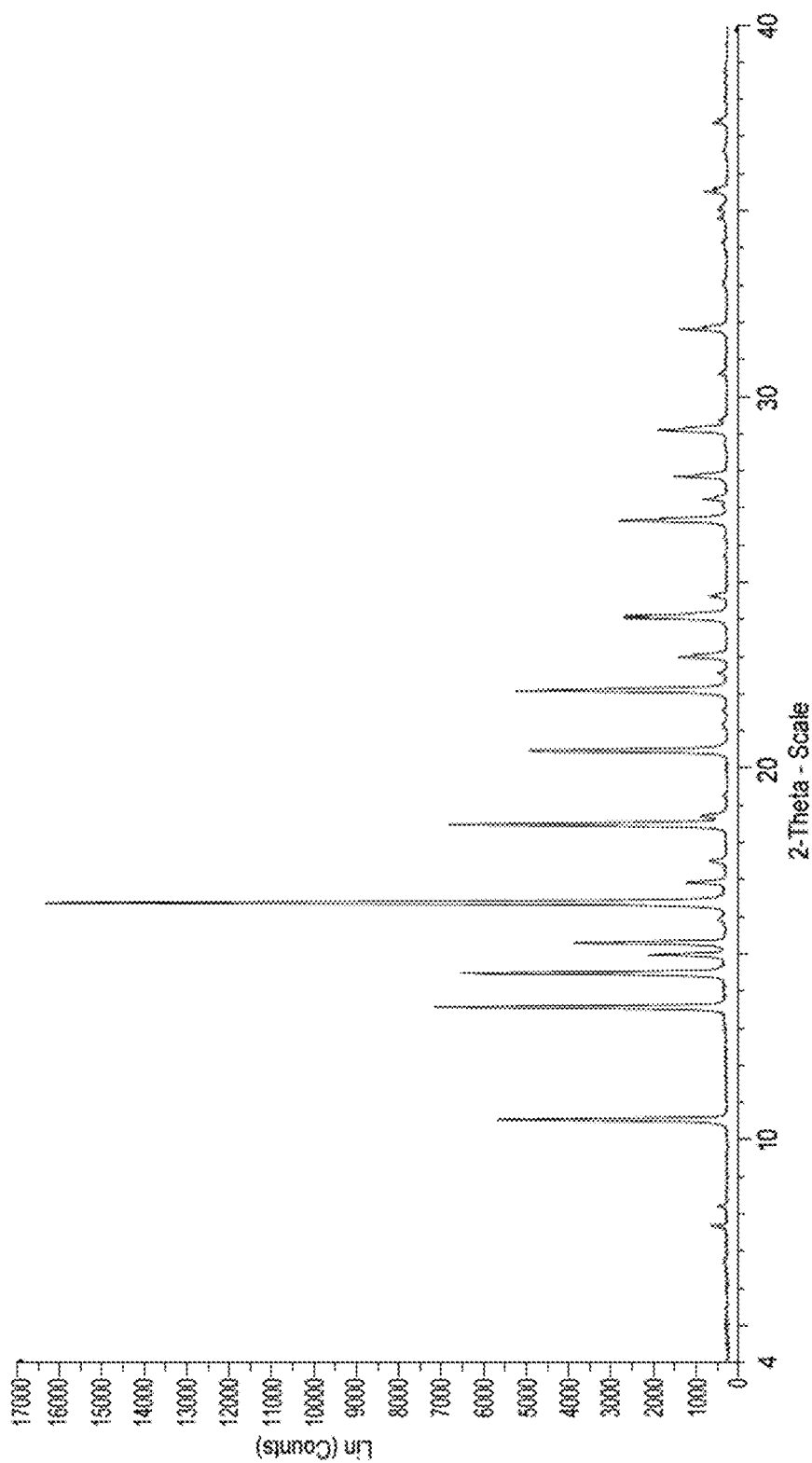
FIG. 3 shows the PXRD spectrum of (3R,4R)-1-benzyl-N,4-dimethylpiperidin-3-amine acetate prepared in Example 6.

The PXRD spectrum of the obtained (3R,4R)-1-benzyl-N,4-dimethylpiperidin-3-amine acetate is shown in FIG. 3. As shown FIG. 3, diffraction peaks exist where the 2θ angles are 7.60±0.2°, 10.49±0.2°, 13.53±0.2°, 14.44±0.2°, 14.99±0.2°, 15.27±0.2°, 16.37±0.2°, 16.89±0.2°, 17.49±0.2°, 18.47±0.2°, 20.47±0.2°, 22.08±0.2°, 23.00±0.2°, 24.07±0.2°, 24.63±0.2°, 26.67±0.2°, 27.24±0.2°, 27.87±0.2°, 29.12±0.2°, 31.84±0.2°, 35.55±0.2°, and 37.42±0.2°.

Figure 4:
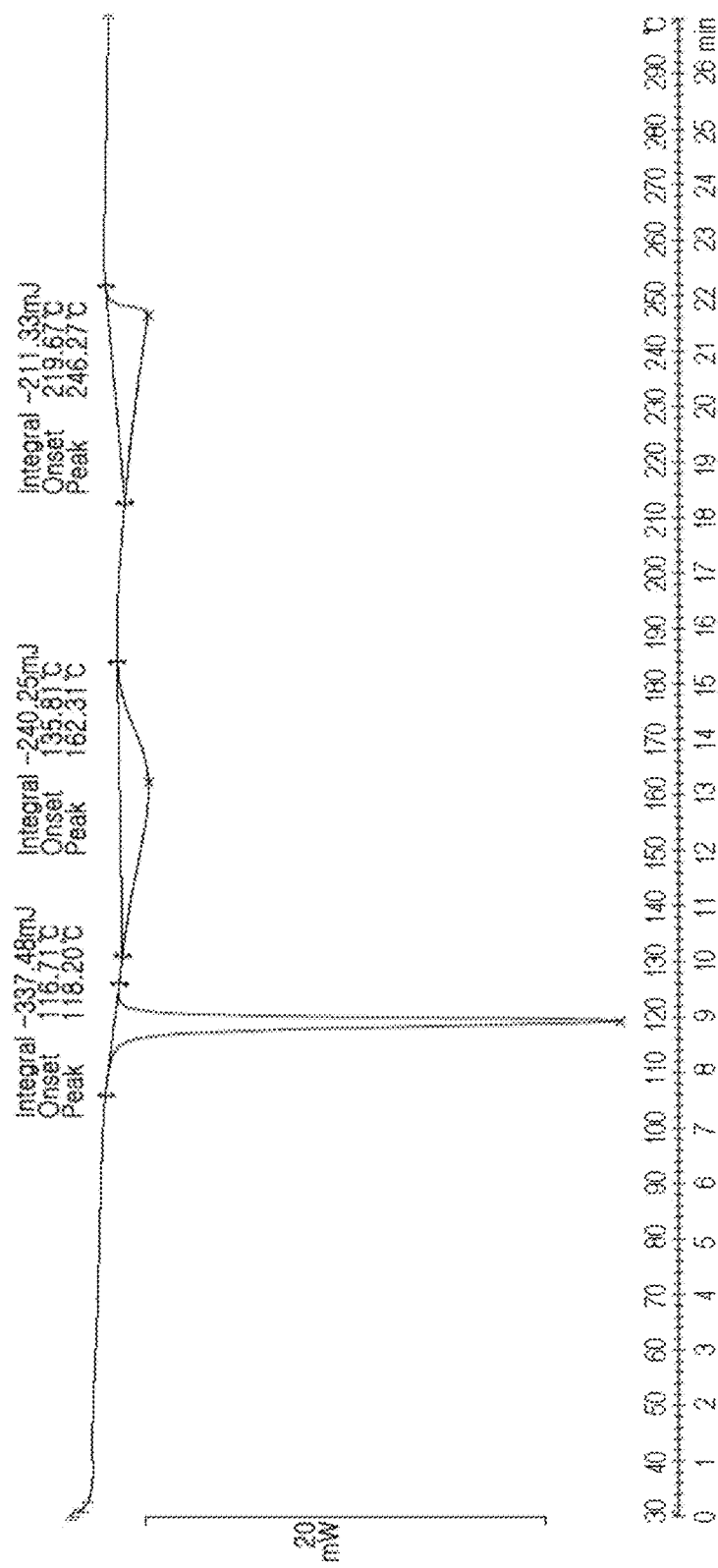
FIG. 4 shows the DSC thermogram of (3R,4R)-1-benzyl-N,4-dimethylpiperidin-3-amine acetate prepared in Example 6.
Figure 5:
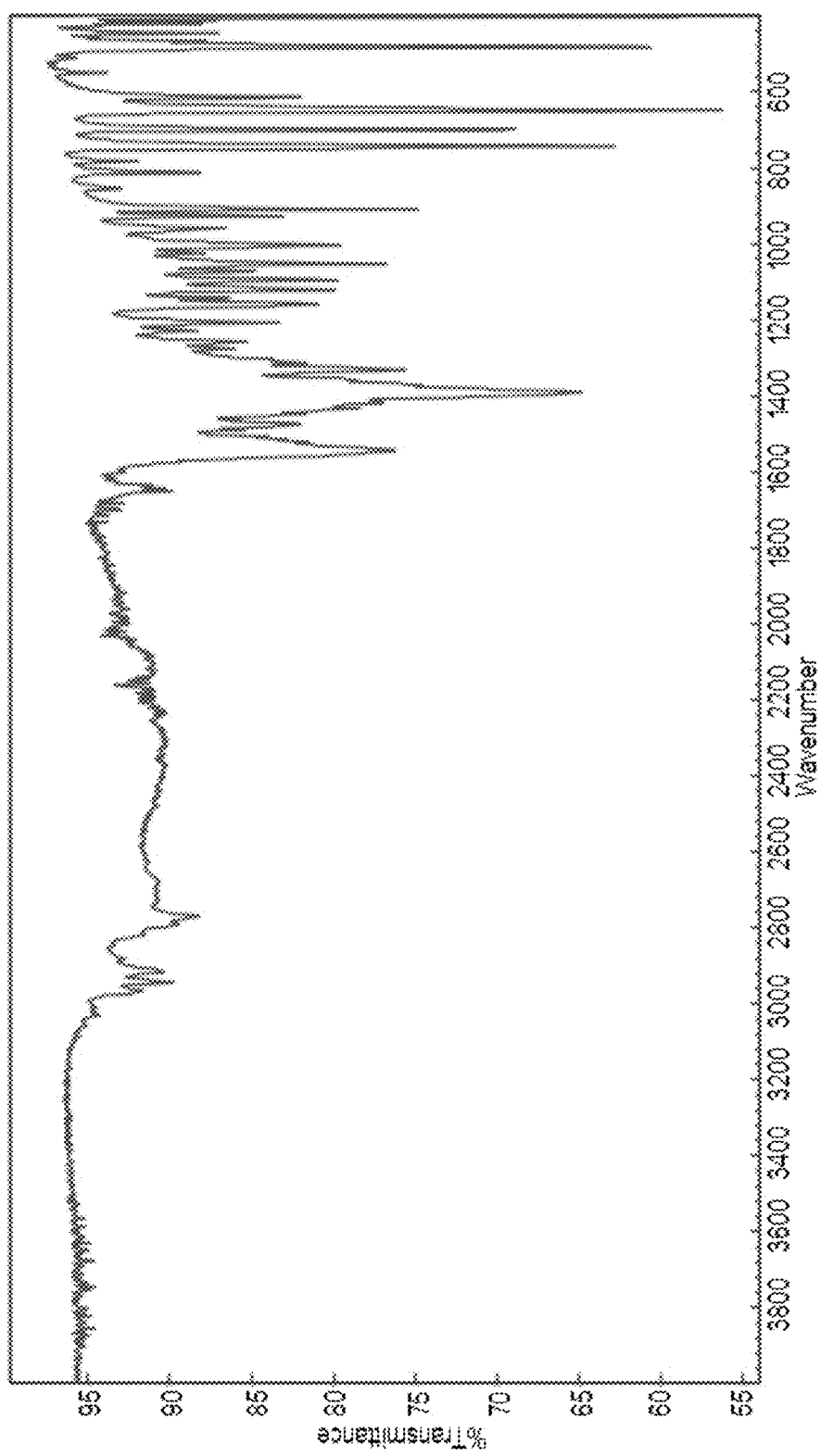
FIG. 5 shows the FT-IR spectrum of (3R,4R)-1-benzyl-N,4-dimethylpiperidin-3-amine acetate prepared in Example 6.
Figure 6:
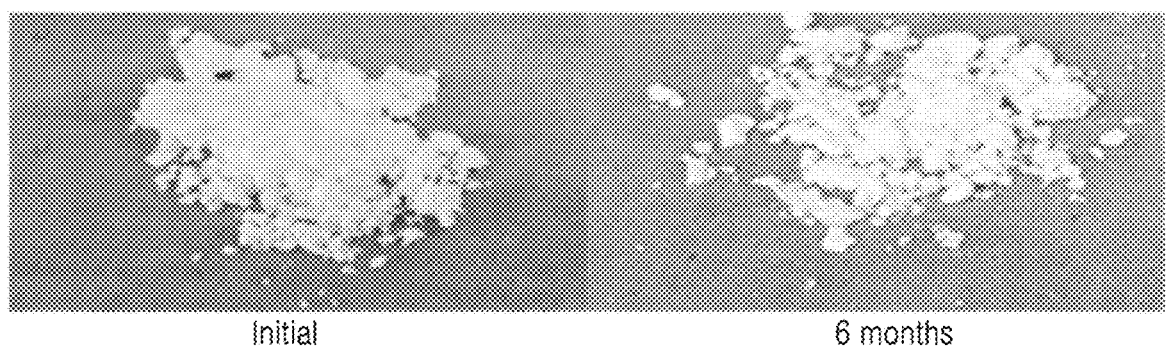
FIG. 6 is the photographs showing the stability test results (appearance), of (3R,4R)-1-benzyl-N,4-dimethylpiperidin-3-amine acetate prepared in Example 7, under the long-term storage condition for 6 months. (Initial: at initial time, 6 months: after 6 months).
Figure 7:
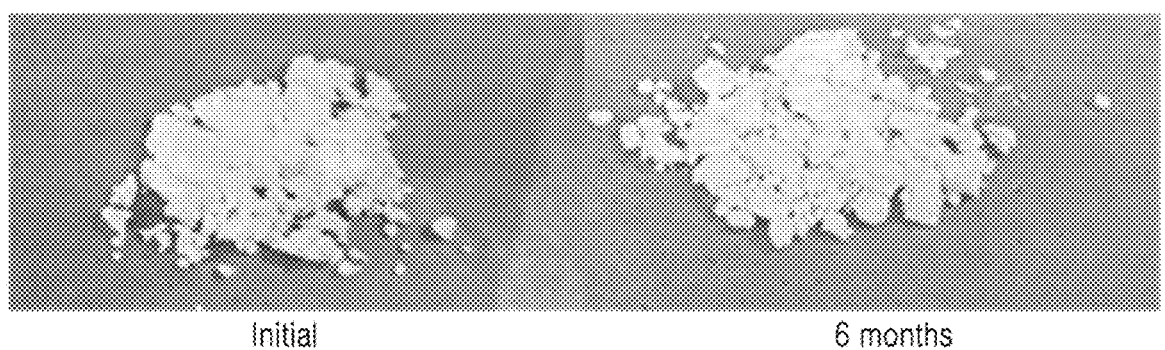
FIG. 7 is the photographs showing the stability test results (appearance), of (3R,4R)-1-benzyl-N,4-dimethylpiperidin-3-amine hydrochloride, under the long-term storage condition for 6 months. (Initial: at initial time, 6 months: after 6 months).
Figure 8:
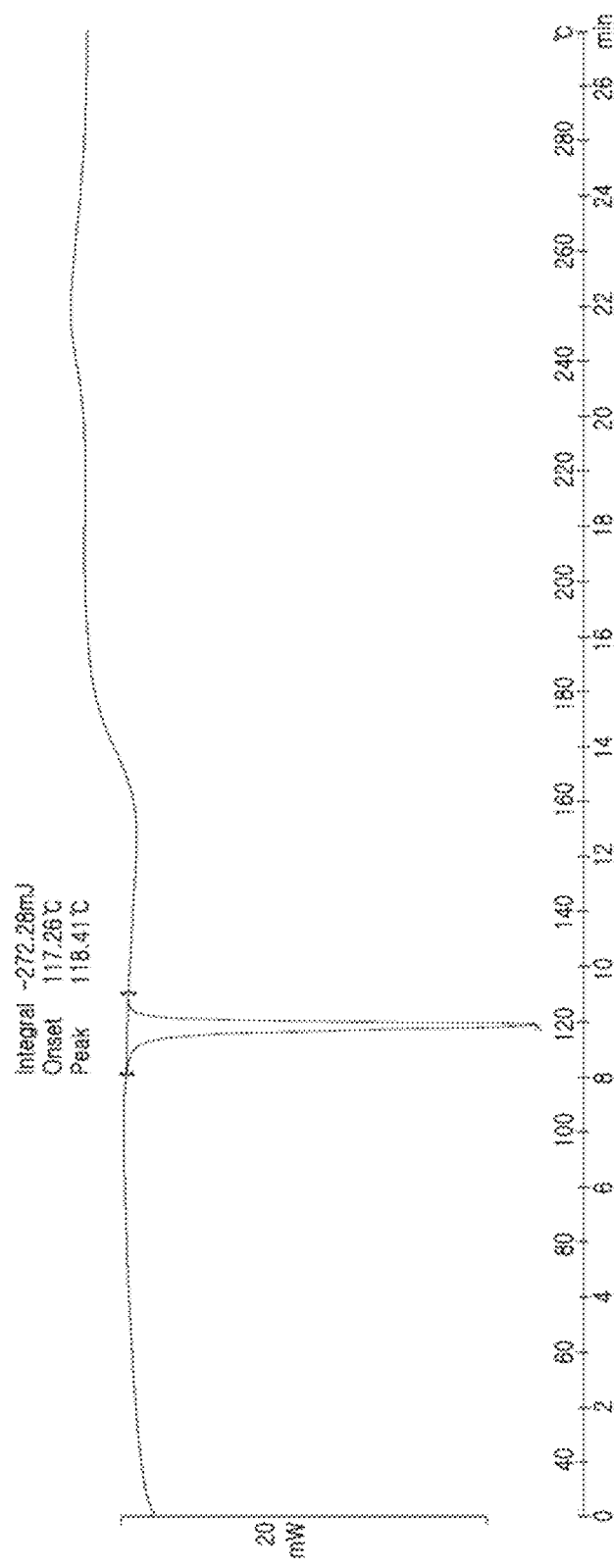
FIG. 8 shows the DSC thermogram of (3R,4R)-1-benzyl-N,4-dimethylpiperidin-3-amine acetate prepared in Example 7, which is obtained by measuring at the initial time of the stability tests.
Figure 9:
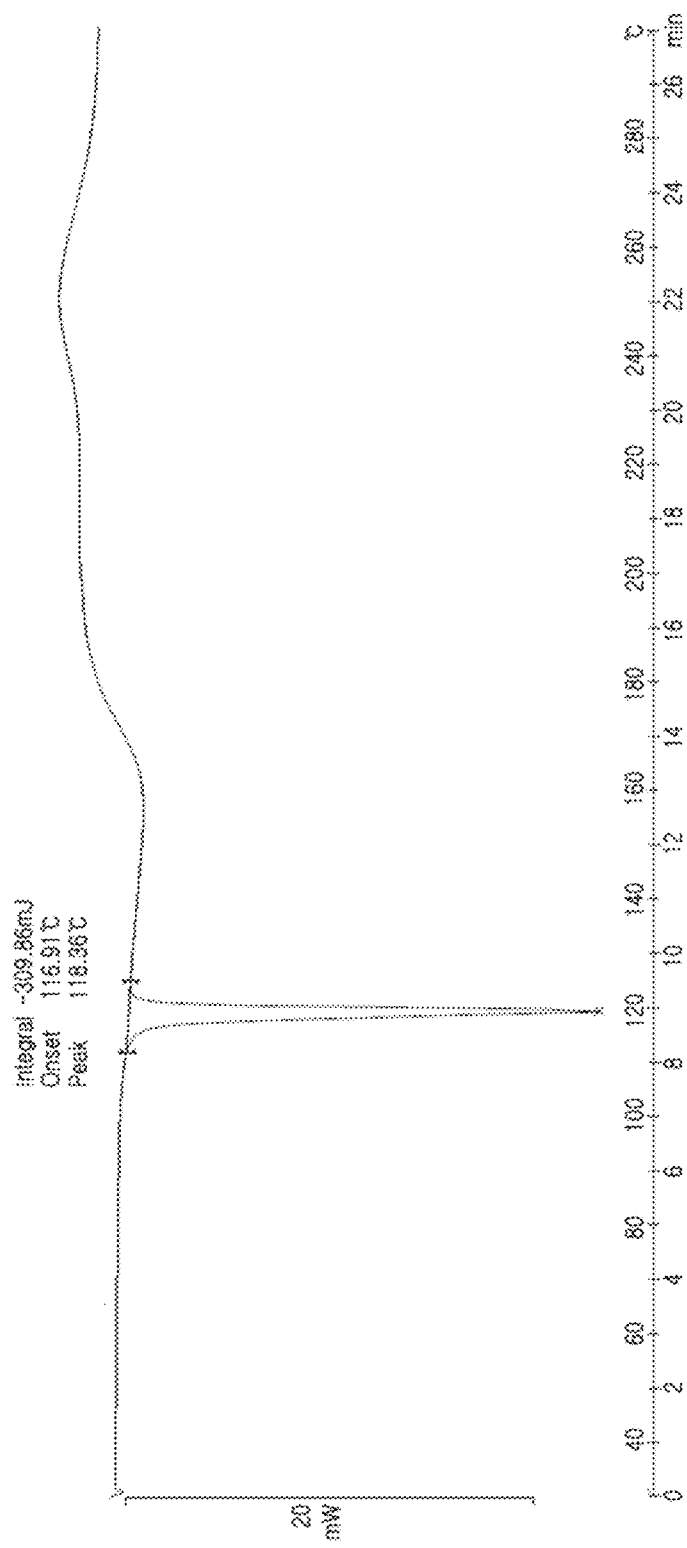
FIG. 9 shows the DSC thermogram obtained by measuring after storing (3R,4R)-1-benzyl-N,4-dimethylpiperidin-3-amine acetate prepared in Example 7 under the long-term storage condition for 6 months.
Figure 10:
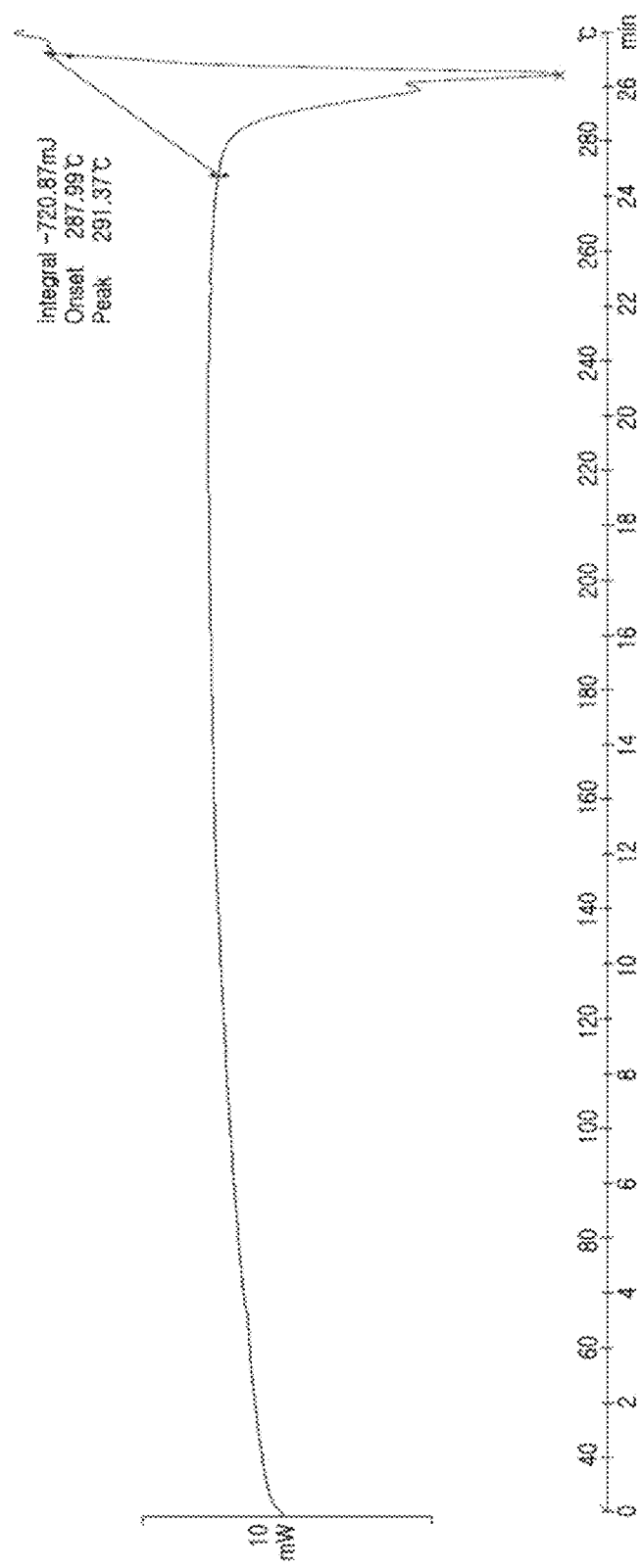
FIG. 10 shows the DSC thermogram of (3R,4R)-1-benzyl-N,4-dimethylpiperidin-3-amine hydrochloride, which is obtained by measuring at the initial time of the stability tests.
Figure 11:
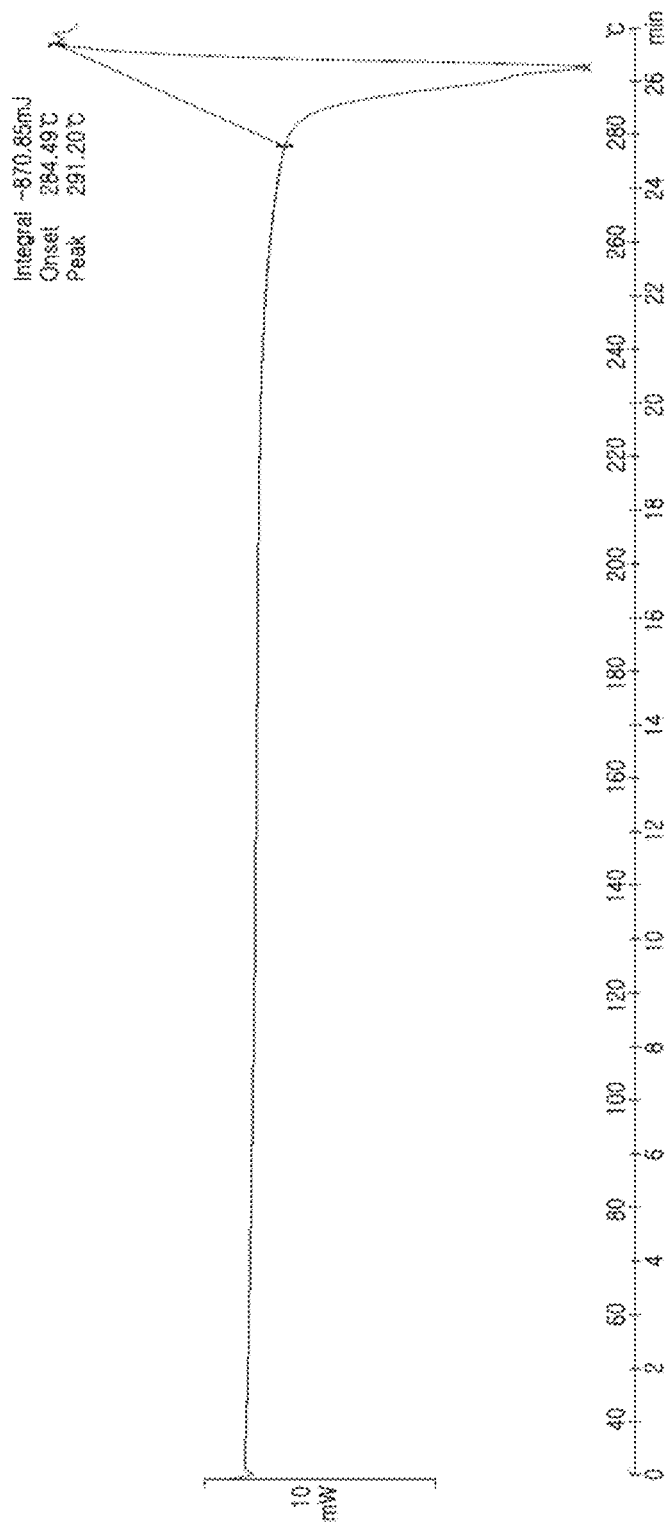
FIG. 11 shows the DSC thermogram obtained by measuring after storing (3R,4R)-1-benzyl-N,4-dimethylpiperidin-3-amine hydrochloride under the long-term storage condition for 6 months.

And also, the DSC thermogram and the FT-IR spectrum of the obtained (3R,4R)-1-benzyl-N,4-dimethylpiperidin-3-amine acetate are shown in FIGS. 4 and 5, respectively. As shown FIG. 5, infrared absorption frequencies (cm$^{-1}$) are 2944, 2917, 1546, 1477, 1395, 1332, 1262, 1211, 1162, 1124, 1099, 1073, 1057, 1006, 961, 930, 911, 815, 784, 746, 702, 652, 616, 485, 448, and 403.

Example 7: Preparation of (3R,4R)-1-benzyl-N,4-dimethylpiperidin-3-amine Acetate A mixture of isopropanol solvate of methyl ((3R,4R)-1-benzyl-4-methylpiperidin-3-yl)carbamate di benzoyl-L-tartrate (1:1:1, chiral purity: 97.20%) (25.0 g) and methyl t-butyl ether (250 mL) was cooled to 10° C. or less and then a 10% potassium carbonate solution (150 mL) was added thereto. The reaction mixture was stirred for about 30 minutes. The organic layer was separated, washed with purified water (25 mL), and then concentrated under reduced pressure. Tetrahydrofuran (35 mL) was added to the concentrate and the resulting mixture was additionally concentrated under reduced pressure. Tetrahydrofuran (163 mL) was added to the concentrate and the resulting mixture was stirred for about 15 minutes. Lithium aluminium hydride (1.99 g) was added to the solution. The reaction mixture was heated under reflux for 3 hours, cooled to −10∼−5° C. An aqueous tetrahydrofuran solution (18 mL, THF:purified water=5:2, (v/v)) was slowly added thereto, while maintaining the internal temperate to 0° C. or less. After the temperature of the reaction mixture was raised to room temperature, the reaction mixture was stirred for about 30 minutes and then filtered. The wet cake was washed with tetrahydrofuran (50 mL). The filtrate and the rinsed solution were combined and then the resulting mixture was concentrated under reduced pressure. Methylethylketone (125 mL) was added to the concentrate, and the resulting mixture was stirred at 35±5° C. for about 15 minutes. Acetic acid (2.21 g) was added to the resulting solution. The reaction mixture was stirred for about 30 minutes, cooled to about 5° C., and then stirred at 0-5° C. for about 1 hour. The product was filtered and then washed with cold methylethylketone (25 mL). The resulting wet cake was dried under vacuum at about 40° C. to obtain 8.45 g of (3R,4R)-1-benzyl-N,4-dimethylpiperidin-3-amine acetate. (Yield: 82.7%)

Chemical purity: 100%
Chiral purity: 99.91%

$^1$H-NMR (400 MHz, DMSO-$d_6$) δ 8.0 (m, 4H), 7.31 (m, 4H), 7.25 (m, 2H), 3.61 (d, 1H), 3.40 (d, 1H), 2.76 (b, 3H), 2.35 (s, 3H), 2.21 (b, 2H), 1.99 (s, 3H), 1.83 (b, 1H), 1.50 (b, 2H), 1.04 (d, 3H)

Example 8: Preparation of (3R,4R)-1-benzyl-N,4-dimethylpiperidin-3-amine Acetate A mixture of isopropanol solvate of methyl ((3R,4R)-1-benzyl-4-methylpiperidin-3-yl)carbamate dibenzoyl-L-tartrate (1:1:1, chiral purity: 95.20%) (25.0 g) and methyl t-butyl ether (250 mL) was cooled to 10° C. or less and then a 10% potassium carbonate solution (150 mL) was added thereto. The reaction mixture was stirred for about 30 minutes. The organic layer was separated, washed with purified water (25 mL), and then concentrated under reduced pressure. Tetrahydrofuran (35 mL) was added to the concentrate and the resulting mixture was additionally concentrated under reduced pressure. Tetrahydrofuran (163 mL) was added to the concentrate and the resulting mixture was stirred for about 15 minutes. Lithium aluminium hydride (1.99 g) was added to the solution. The reaction mixture was heated under reflux for 3 hours, cooled to −10~−5° C. An aqueous tetrahydrofuran solution (18 mL, THF:purified water=5:2, (v/v)) was slowly added thereto, while maintaining the internal temperate to 0° C. or less. After the temperature of the reaction mixture was raised to room temperature, the reaction mixture was stirred for about 30 minutes and then filtered through a celite pad. The wet cake was washed with tetrahydrofuran (50 mL). The filtrate and the rinsed solution were combined and then the resulting mixture was concentrated under reduced pressure. Methylethylketone (125 mL) was added to the concentrate and the resulting mixture was stirred at 35±5° C. for about 15 minutes. Acetic acid (2.21 g) was added to the resulting solution. The reaction mixture was stirred for about 30 minutes, cooled to about 5° C., and then stirred at 0-5° C. for about 1 hour. The product was filtered and then washed with cold methylethylketone (25 mL). The resulting wet cake was dried under vacuum at about 40° C. to obtain 8.06 g of (3R,4R)-1-benzyl-N,4-dimethylpiperidin-3-amine acetate. (Yield: 78.9%)

Chemical purity: 100%
Chiral purity: 99.87%
$^1$H-NMR (400 MHz, DMSO-d$_6$) δ 8.0 (m, 4H), 7.31 (m, 4H), 7.25 (m, 2H), 3.61 (d, 1H), 3.40 (d, 1H), 2.76 (b, 3H), 2.35 (s, 3H), 2.21 (b, 2H), 1.99 (s, 3H), 1.83 (b, 1H), 1.50 (b, 2H), 1.04 (d, 3H)

Example 9: Preparation of (3R,4R)-(1-benzyl-4-methylpiperidin-3-yl)-2-chloro-N-methyl-(7H-pyrrolo[2,3-d]pyrimidin-4-yl)-amine A mixture of (3R,4R)-1-benzyl-N,4-dimethylpiperidin-3-amine acetate (chiral purity: 99.98%) (50.0 g) and 5% sodium hydrogen carbonate solution (1.5 L) was stirred for about 30 minutes. 2,4-Dichloro-7H-pyrrolo[2,3-d]pyrimidine (33.8 g) was added to the reaction mixture, which was then stirred at 100±5° C. for 12 hours. The reaction mixture was cooled to room temperature, stirred for about 1 hour, and then filtered. The resulting product was washed with purified water (500 mL). The resulting wet cake was dried under vacuum at about 50° C. to obtain 64.1 g of (3R,4R)-(1-benzyl-4-methylpiperidin-3-yl)-2-chloro-N-methyl-(7H-pyrrolo[2,3-d]pyrimidin-4-yl)-amine. (Yield: 97%)

Chemical purity: 98%
Chiral purity: 99.98%
$^1$H-NMR (400 MHz, DMSO-d$_6$) δ 11.80 (s, 1H), 7.31 (m, 4H), 7.21-7.25 (m, 1H), 7.12 (s, 1H), 6.58 (b, 1H), 4.99 (b, 1H), 3.38-3.50 (m, 5H), 2.77-2.81 (m, 1H), 2.64 (b, 1H), 2.53-2.55 (m, 1H), 2.24 (b, 1H), 2.18 (b, 1H), 1.60-1.63 (m, 2H), 0.87 (d, 3H)

Example 10: Preparation of (3R,4R)-(4-methylpiperidin-3-yl)-N-methyl-(7H-pyrrolo[2,3-cl]pyrimidin-4-yl)-amine (3R,4R)-(1-benzyl-4-methylpiperidin-3-yl)-2-chloro-N-methyl-(7H-pyrrolo[2,3-d]pyrimidin-4-yl)-amine (chemical purity: 99.7%, chiral purity: 99.98%) (450.0 g) and purified water (4.5 L) were added to a hydrogenation reactor. 10% Palladium hydroxide on carbon catalyst (20.5 g) and a hydrochloric acid solution (53 mL) were added thereto. The hydrogenation reactor was filled with hydrogen, pressurized to 30 psi, and stirred at 70±5° C. for 3 hours. The reaction mixture was cooled to room temperature and hydrogen gas was removed therefrom by nitrogen replacement. The reaction mixture was filtered through a celite pad. The wet cake was washed with purified water (0.9 L). Dichloromethane (4.5 L) was added to the combined filtrate and washing solution, which was then stirred for about 30 minutes. The pH of the reaction mixture was adjusted to about pH 10-12 with a 50% sodium hydroxide solution. The organic layer was separated and then concentrated under reduced pressure to obtain 287 g of (3R,4R)-(4-methylpiperidin-3-yl)-N-methyl-(7H-pyrrolo[2,3-d]pyrimidin-4-yl)-amine. (Yield: 96%)

Chemical purity: 99.8%
Chiral purity: 99.98%
$^1$H-NMR (400 MHz, DMSO-d$_6$) δ 11.61 (s, 1H), 8.08 (s, 1H), 7.11 (d, 1H), 6.52 (d, 1H), 4.78 (s, 1H), 3.31 (s, 3H), 3.09-3.14 (m, 1H), 2.78-2.84 (m, 2H), 2.74 (m, 1H), 2.29-2.32 (m, 1H), 1.70-1.76 (m, 1H), 1.44-1.48 (m, 1H), 0.96 (d, 3H)

Example 11: Preparation of Tofacitinib

To a mixture of (3R,4R)-(4-methylpiperidin-3-yl)-N-methyl-(7H-pyrrolo[2,3-d]pyrimidin-4-yl)-amine (chemical purity: 99.8%, chiral purity: 99.98%) (270.0 g) and tetrahydrofuran (2.7 L), were added ethyl cyanoacetate (187 g) and 1,8-diazabicyclo[5,4,0]undec-7-ene (168 g). The reaction mixture was stirred for 24 hours while maintaining the reaction temperature to 20-30° C. Purified water (5.4 L) was added to the reaction mixture, the pH of which was adjusted to pH 7-8 with a 20% hydrochloric acid solution. The reaction mixture was stirred for 12 hours and then filtered. The resulting product was washed with a 33% aqueous tetrahydrofuran solution (0.8 L). The resulting wet cake was dried at about 60° C. to obtain 267 g of tofacitinib. (Yield: 78%)

Chemical purity: 99.2%
Chiral purity: 99.98%
$^1$H-NMR (400 MHz, DMSO-d$_6$) δ 11.67 (s, 1H), 8.11 (d, 1H), 7.14 (s, 1H), 6.56 (s, 1H), 4.85 (s, 1H), 3.62-4.15 (m, 4.5H), 3.37-3.43 (m, 1.5H), 3.25 (s, 3H), 2.38-2.42 (m, 1H), 1.68-1.72 (m, 1H), 1.53-1.59 (m, 1H), 0.99-1.03 (m, 3H)

Experimental Example: Stability Test

Stability tests under the long-term storage condition of the following table 1 were performed for the (3R,4R)-1-benzyl-N,4-dimethylpiperidin-3-amine acetate prepared in Example 7 and the (3R,4R)-1-benzyl-N,4-dimethylpiperidin-3-amine hydrochloride prepared according to the known methods.

TABLE 1

| | Long-term storage condition |
|---|---|
| Temperature | 25 ± 2° C. |
| Relative humidity | 60 ± 5 RH % |
| Vessel | 20 mL glass vial |
| Sampling | Initial/after 6 months |

The stability test results under the long-term storage conditions are shown in FIGS. 6 to 11. The table 2 summarizes the results thereof.

TABLE 2

|  | (3R,4R)-1-benzyl-N,4-dimethylpiperidin-3-amine acetate | | (3R,4R)-1-benzyl-N,4-dimethylpiperidin-3-amine hydrochloride | |
| --- | --- | --- | --- | --- |
|  | Initial | After 6 months | Initial | After 6 months |
| Appearance (color) | White solid | White solid | White solid | White solid |
| DSC peak (° C.) | 118.4° C. | 118.4° C. | 291.4° C. | 291.2° C. |
| Chemical purity (%) | 100.0% | 100.0% | 99.1% | 99.1% |
| Chiral purity (%) | 99.9% | 99.9% | 100.0% | 99.9% |

As can be seen from the above stability test results, the (3R,4R)-1-benzyl-N,4-dimethylpiperidin-3-amine acetate prepared according to the present invention does not show any significant changes in appearance, chemical purity, chiral purity, and DSC peak temperature, between at the initial time and at the end time of the test.

The invention claimed is:

1. A process for preparing (3R,4R)-1-benzyl-N,4-dimethylpiperidin-3-amine acetate, the process of which comprises:
   (a) reacting racemic methyl (1-benzyl-4-methylpiperidin-3-yl) carbamate and dibenzoyl-L-tartaric acid by heating under reflux in a solvent selected from the group consisting of isopropanol, an aqueous solution of isopropanol, and a mixed solvent of isopropanol and an organic solvent, followed by cooling to prepare isopropanol solvate of methyl ((3R,4R)-1-benzyl-4-methylpiperidin-3-yl) carbamate dibenzoyl-L-tartrate; and
   (b) reacting the isopropanol solvate of methyl ((3R,4R)-1-benzyl-4-methylpiperidin-3-yl) carbamate dibenzoyl-L-tartrate prepared in Step (a) with a base to convert to methyl ((3R,4R)-1-benzyl-4-methylpiperidin-3-yl) carbamate; reducing the methyl ((3R,4R)-1-benzyl-4-methylpiperidin-3-yl) carbamate to prepare (3R,4R)-1-benzyl-N,4-dimethylpiperidin-3-amine; and then reacting the (3R,4R)-1-benzyl-N,4-dimethylpiperidin-3-amine with acetic acid to prepare (3R,4R)-1-benzyl-N,4-dimethylpiperidin-3-amine acetate.

2. The process according to claim 1, wherein the mixed solvent of isopropanol and an organic solvent is a mixed solvent of isopropanol and an organic solvent selected from the group consisting of methanol, ethanol, n-propanol, acetone, methylethylketone, methyl acetate, ethyl acetate, tetrahydrofuran, 2-methyltetrahydrofuran and acetonitrile.

3. The process according to claim 1, wherein Step (a) further comprises recrystallizing the isopropanol solvate of methyl ((3R,4R)-1-benzyl-4-methylpiperidin-3-yl) carbamate dibenzoyl-L-tartrate in a mixed solvent of isopropanol and methanol or a mixed solvent of isopropanol and ethanol.

4. The process according to claim 1, wherein the cooling in Step (a) is performed to a temperature ranging from 0 to 55° C.

5. The process according to claim 1, wherein the base used in Step (b) is one or more selected from the group consisting of potassium carbonate, potassium hydrogen carbonate, sodium carbonate, sodium hydrogen carbonate, sodium hydroxide, and potassium hydroxide.

6. The process according to claim 1, wherein the reducing of Step (b) is carried out by using one or more reducing agents selected from the group consisting of lithium aluminium hydride, lithium bis (2-methoxyethoxy) aluminum hydride, and sodium hydride.

7. The process according to claim 1, wherein the reaction of the (3R,4R)-1-benzyl-N,4-dimethylpiperidin-3-amine with acetic acid is carried out in a solvent selected from the group consisting of methanol, ethanol, isopropanol, n-propanol, acetone, methylethylketone, methyl acetate, ethyl acetate, isopropyl acetate, tetrahydrofuran, 2-methyltetrahydrofuran, acetonitrile, and a mixed solvent thereof.

8. Isopropanol solvate of methyl ((3R,4R)-1-benzyl-4-methylpiperidin-3-yl) carbamate dibenzoyl-L-tartrate.

9. (3R,4R)-1-benzyl-N,4-dimethylpiperidin-3-amine acetate.

10. A process for preparing tofacitinib or a pharmaceutically acceptable salt thereof, the process of which comprises:
   (i) preparing (3R,4R)-1-benzyl-N,4-dimethylpiperidin-3-amine acetate according to the process according to claim 1;
   (ii) reacting the (3R,4R)-1-benzyl-N,4-dimethylpiperidin-3-amine or a salt thereof with 2,4-dichloro-7H-pyrrolo[2,3-d]pyrimidine to prepare (3R,4R)-(1-benzyl-4-methylpiperidin-3-yl)-2-chloro-N-methyl-(7H-pyrrolo[2,3-d]pyrimidin-4-yl)-amine;
   (iii) performing debenzylation of the (3R,4R)-(1-benzyl-4-methylpiperidin-3-yl)-2-chloro-N-methyl-(7H-pyrrolo[2,3-d]pyrimidin-4-yl)-amine to prepare (3R,4R)-(4-methylpiperidin-3-yl)-N-methyl-(7H-pyrrolo[2,3-d]pyrimidin-4-yl)-amine; and
   (iv) reacting the (3R,4R)-(4-methylpiperidin-3-yl)-N-methyl-(7H-pyrrolo[2,3-d]pyrimidin-4-yl)-amine with ethyl cyanoacetate to prepare tofacitinib.

* * * * *